(12) United States Patent
Farazi et al.

(10) Patent No.: US 9,162,067 B1
(45) Date of Patent: Oct. 20, 2015

(54) METHODS AND DEVICES FOR MONITORING MYOCARDIAL ELECTRO-MECHANICAL STABILITY

(75) Inventors: Taraneh Ghaffari Farazi, San Jose, CA (US); Eric Falkenberg, Simi Valley, CA (US); Euljoon Park, Valencia, CA (US)

(73) Assignee: Pacesetter, Inc., Sunnyvale, CA (US)

(*) Notice: Subject to any disclaimer, the term of this patent is extended or adjusted under 35 U.S.C. 154(b) by 0 days.

(21) Appl. No.: 11/925,273

(22) Filed: Oct. 26, 2007

(51) Int. Cl.
*A61N 1/365* (2006.01)
*A61N 1/37* (2006.01)
*A61B 5/0452* (2006.01)
*A61N 1/362* (2006.01)

(52) U.S. Cl.
CPC .............. *A61N 1/3702* (2013.01); *A61B 5/0452* (2013.01); *A61N 1/3627* (2013.01); *A61N 1/36514* (2013.01)

(58) Field of Classification Search
USPC .................................................. 600/513–519
See application file for complete search history.

(56) References Cited

U.S. PATENT DOCUMENTS

| | | | |
|---|---|---|---|
| 4,984,572 A | 1/1991 | Cohen | |
| 5,921,940 A | 7/1999 | Verrier et al. | |
| 6,253,107 B1 | 6/2001 | Albrecht et al. | |
| 6,823,213 B1 | 11/2004 | Norris et al. | |
| 6,915,156 B2 | 7/2005 | Christini et al. | |
| 6,915,157 B2 | 7/2005 | Bennett et al. | |
| 2003/0158584 A1 | 8/2003 | Cates et al. | |
| 2003/0233132 A1* | 12/2003 | Pastore et al. | 607/17 |
| 2004/0162497 A1* | 8/2004 | Bennett et al. | 600/513 |
| 2005/0004608 A1 | 1/2005 | Bullinga | |
| 2005/0191678 A1* | 9/2005 | Lapointe et al. | 435/6 |

(Continued)

FOREIGN PATENT DOCUMENTS

| | | |
|---|---|---|
| EP | 0666724 A4 | 3/1994 |
| EP | 0666724 B1 | 3/1994 |
| EP | 0739181 A4 | 9/2001 |

(Continued)

OTHER PUBLICATIONS

Clancy, et al. "A simple electrical-mechanical model of the heart applied to the study of electrical-mechanical alternans" 1991, IEEE Trans Biomed Eng., 38(6), pp. 551-560.*

(Continued)

*Primary Examiner* — Erica Lee
(74) *Attorney, Agent, or Firm* — Theresa A. Raymer

(57) ABSTRACT

Embodiments of the present invention relate to implantable systems, and methods for use therewith, for monitoring myocardial electro-mechanical stability, and responding to the same. One or more signal indicative of electrical functioning of a patient's heart is obtained, as is one or more signal indicative of mechanical functioning of the patient's heart. The patient's myocardial electrical stability is monitored based on the one or more signal indicative of electrical functioning of the patient's heart, and the patient's myocardial mechanical stability is monitored based on the one or more signal indicative of mechanical functioning of the patient's heart. Based on both the myocardial electrical stability and myocardial mechanical stability, the patient's risk of an adverse cardiac event is monitored. Further, when the patient is at risk of an adverse cardiac event, a response is triggered that is specific to both the myocardial electrical stability and the myocardial mechanical stability. This abstract is not intended to be a complete description of, or limit the scope of, the invention.

26 Claims, 5 Drawing Sheets

(56) References Cited

U.S. PATENT DOCUMENTS

2006/0116596 A1* 6/2006 Zhou et al. .................. 600/516
2008/0269627 A1* 10/2008 Cho et al. .................... 600/521

FOREIGN PATENT DOCUMENTS

| EP | 0739181 B1 | 9/2001 |
| WO | 9406350 A1 | 3/1994 |
| WO | 9515116 A1 | 6/1995 |
| WO | 2004073513 A2 | 9/2004 |
| WO | 2004073513 A3 | 9/2004 |

OTHER PUBLICATIONS

Surawicz, B. and Fisch, C. "Cardiac Alternans: Diverse Mechanisms and Clinical Manifestations" JACC vol. 20, No. 2. Aug. 1992: 483-99.*

* cited by examiner

METHODS AND DEVICES FOR MONITORING MYOCARDIAL ELECTRO-MECHANICAL STABILITY

FIELD OF THE INVENTION

The present invention generally relates methods and devices that are capable of monitoring myocardial electro-mechanical stability, including detecting electrical and mechanical alternans.

BACKGROUND

Electrical alternans relate to the differences in electrical potential at corresponding points between alternate heartbeats. T-wave alternans or alternation is a regular or beat-to-beat variation of the ST-segment or T-wave of an electrocardiogram (ECG) which repeats itself every two beats and has been linked to underlying cardiac electrical instability. Typically, by enumerating all consecutive heart beats of a patient, beats with an odd number are referred to as "odd beats" and beats with an even number are referred to as "even beats." A patient's odd and even heartbeats may exhibit different electrical properties of diagnostic significance which can be detected from an ECG.

The presence of these electrical alternans is significant because patients at increased risk for ventricular arrhythmia's commonly exhibit alternans in the ST-segment and the T-wave of their ECG. Clinicians may therefore use these electrical alternans as a noninvasive marker of vulnerability to ventricular tachyarrhythmias. The term T-wave alternans (TWA) is used broadly to denote electrical alternans such as these. It should be understood that the term encompasses both the alternans of the T-wave segment and the ST-segment of an ECG.

T-wave alternans (TWA) has been demonstrated in many studies as a strong predictor of mortality, independent of left ventricular ejection fraction (LVEF). More specifically, it has become well known that T-wave alternans has predictive value for arrhythmic events such as tachyarrhythmias. Additionally, T-wave alternans has been determined to be an indicator of various forms of disordered ventricular repolarization, including disorders found in patients with cardiomyopathy, mild to moderate heart failure, and congestive heart failure.

Mechanical alternans, also known as mechanical pulse alternans (MPA), relate to the situation where alternating contractions of the heart exhibit alternating values of contraction force or magnitude that cause ejected blood to exhibit similar alternating values of diastolic pressure amplitude. More specifically, the presence of mechanical alternans can be defined by a consistent alternation in peak left ventricular (LV) pressure, or dP/dt, in successive beats.

Visible mechanical alternans have been observed in patients with severe congestive heart failure caused by global left ventricular dysfunction, and is considered to be a terminal sign in this population. Mechanical alternans is characterized by alternating strong and weak beats with a substantially constant beat-to-beat interval. Although its precise origin remains unclear, studies have suggested a link to abnormal intracellular Ca2+ cycling in failing cardiomyocytes. Studies have also shown that prevalence of mechanical alternans increases with exercise and dobutamine loading compared to rest, indicating that mechanical alternan is a rate dependent phenomenon.

Electrical alternans and mechanical alternans, or more generally, myocardial electrical stability and myocardial mechanical stability, are generally monitored separately. Thus, a comprehensive understanding of myocardial stability is not typically achieved.

BRIEF SUMMARY OF THE INVENTION

The inventors of the present invention believe it would be beneficial to monitor both electrical and mechanical myocardial characteristics to obtain a more comprehensive understanding of myocardial stability and how to respond to the same. Embodiments of the present invention relate to systems, and methods for use therewith, for monitoring myocardial electro-mechanical stability, and responding thereto. Such systems can be implantable, non-implantable, or combinations thereof.

In accordance with certain embodiments, one or more signal indicative of electrical functioning of a patient's heart is obtained, as is one or more signal indicative of mechanical functioning of the patient's heart. The patient's myocardial electrical stability is monitored based on the one or more signal indicative of electrical functioning of the patient's heart, and the patient's myocardial mechanical stability is monitored based on the one or more signal indicative of mechanical functioning of the patient's heart. Based on both the myocardial electrical stability and myocardial mechanical stability, the patient's risk of an adverse cardiac event is monitored. Further, when the patient is at risk of an adverse cardiac event, a response can be triggered that is specific to both the myocardial electrical stability and the myocardial mechanical stability.

In accordance with an embodiment of the present invention, the one or more signal indicative of electrical functioning of the patient's heart includes an intra cardiac electrogram signal (IEGM), and the one or more signal indicative of mechanical functioning of the patient's heart includes a pressure signal. Alternatively, the one or more signal indicative of mechanical functioning of the patient's heart can include one or more of the following: a signal representative of ventricular pressure obtained from a pressure transducer within a ventricle; a signal representative of contraction strength obtained from an accelerometer; a signal representative of blood flow rate obtained from a blood flow transducer; a signal representative of heart sounds obtained from a microphone or an accelerometer that responds to acoustic vibrations transmitted through body fluids; a signal representative of blood volume obtained using an impedance measuring circuit; a signal representative of pulse pressure obtained using a photo-plethysmography sensor; or a signal representative of venous oxygen saturation obtained using an SVO2 sensor.

In accordance with specific embodiments, the response to be triggered is selecting from at least two different responses, when the patient is at risk of an adverse cardiac event. For example, the different responses can involve delivering different types of cardiac therapy and/or notifying different types of caregivers.

Myocardial electrical stability can be monitored by monitoring a degree of electrical alternans based on the one or more signal indicative of electrical functioning of the patient's heart, and monitoring the patient's myocardial electrical stability based on the degree of electrical alternans. Myocardial mechanical stability can be monitored by monitoring a degree of mechanical alternans based on the one or more signal indicative of mechanical functioning of the patient's heart, and monitoring the patient's myocardial mechanical stability based on the degree of mechanical alternans. Accordingly, a response can be triggered that is specific to both the degree of electrical alternans and the degree of mechanical alternans. For example, a first response can be triggered if electrical alternans are present but mechanical alternans are not present; a second response can be triggered if mechanical alternans are present but electrical alternans are not present; and a third response can be triggered if both electrical and mechanical alternans are present.

Specific embodiments of the present invention also relate to determining a myocardial electro-mechanical stability score, which can be indicative a patient's risk of an adverse cardiac event. Further, the patient's myocardial ischemic burden can also be determined, and used to determine the myocardial electro-mechanical stability score. A response that is triggered can be based on such a score.

This description is not intended to be a complete description of, or limit the scope of, the invention. Other features, aspects, and objects of the invention can be obtained from a review of the specification, the figures, and the claims.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Exemplary ICD

Figure 1:
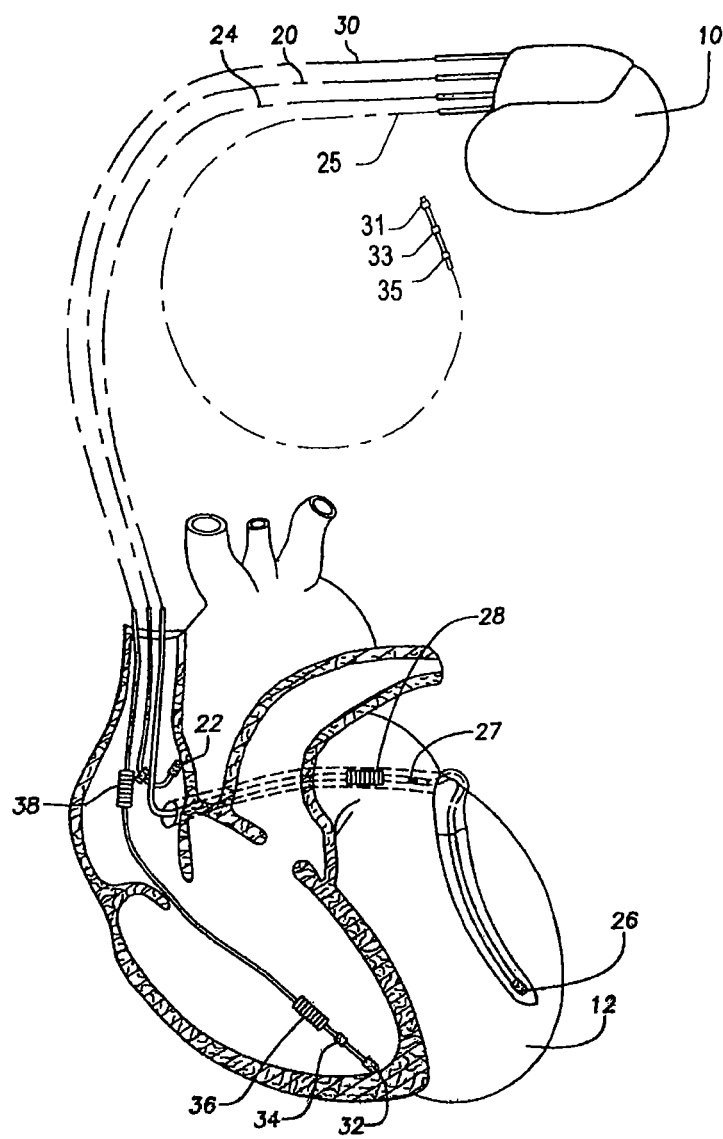
FIG. 1 is a simplified diagram illustrating an exemplary ICD in electrical communication with a patient's heart.
Figure 2:
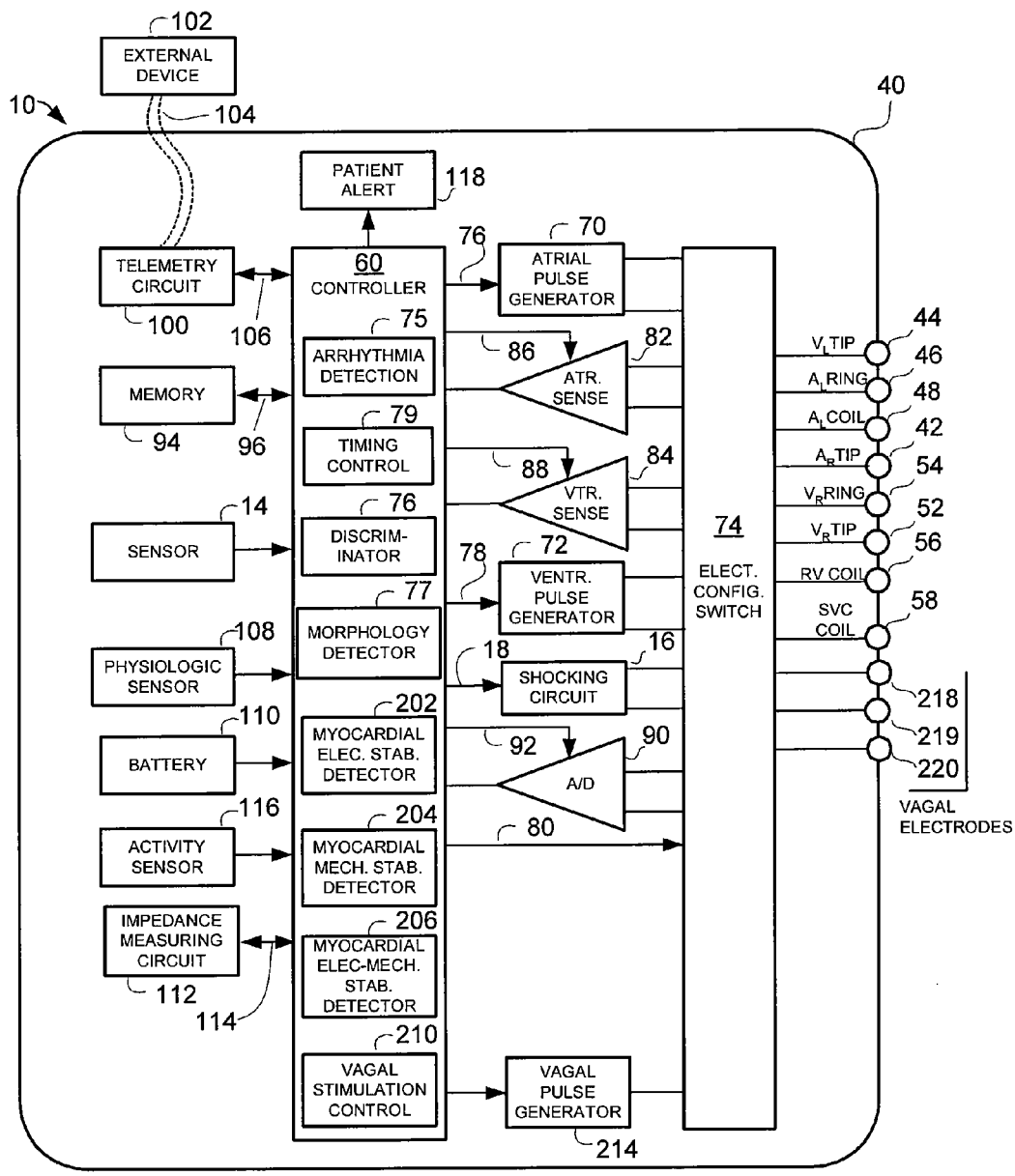
FIG. 2 is a functional block diagram of an exemplary ICD that can provide cardioversion, defibrillation, and pacing stimulation in four chambers of a heart, and monitor and respond to myocardial electro-mechanical stability in accordance with embodiments of the present invention.

Before describing the invention in detail, it is helpful to describe an example environment in which the invention may be implemented. The present invention is particularly useful in the environment of an implantable cardiac device that can monitor mechanical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

One of the above described leads (or a further lead) can also connect a further sensor (not specifically shown in FIG. 1, but shown as sensor 14 in FIG. 2) to the ICD 10, where the further sensor 14 is capable of measuring the mechanical functioning of the heart, or a surrogate thereof. In one embodiment, the sensor 14 is a pressure transducer that obtains measures of ventricular pressure. In another embodiment, the sensor 14 is an accelerometer that obtains measures of contraction strength. In a further embodiment, the sensor 14 is a blood flow transducer that obtains measures of blood flow rate. In still another embodiment, the sensor 14 is an acoustic transducer that obtains measures of heart sounds. Such an acoustic transducer can be, e.g., a microphone or an accelerometer that responds to acoustic vibrations transmitted through body fluids, to thereby detect alternating loud and soft sounds. In a further embodiment, the sensor 14 is an impedance measuring circuit having voltage sense electrodes to measure volumetric alternans, which is a surrogate of mechanical alternans. In still another embodiment, the sensor 14 is a photoplethysmography (PPG) sensor that measures pulse pressure. In a further embodiment, the sensor is a venous oxygen saturation (SVO2) sensor that measures venous oxygen saturation levels, which are believed to be indicative of mechanical functioning of the heart. These are just some examples of sensors that are capable of measuring the mechanical functioning of the heart, or a surrogate thereof. Other types of sensors capable of measuring the mechanical functioning of the heart, or a surrogate thereof, are also within the scope of the present invention.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts. Additionally, where the sensor 14 is connected to the ICD by its own lead, the connector can include a terminal 222, which is configured for connecting the sensor 14 to the ICD. It is also possible that the sensor 14 is integrated with the housing 40, and thus does not need to be connected via a terminal.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the ICD's and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting mechanical alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram (IEGM) signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes. Each cycle of such IEGM signals, which corresponds to a heart beat, includes a P wave that is a normally small positive wave caused by the beginning of a heart beat. Following the P wave there is a portion which is substantially constant in amplitude. The QRS complex of the IEGM then normally occurs after the substantially constant portion, beginning with a Q wave that is normally a small negative deflection, which is then immediately succeeded by the R wave that is a rapid positive deflection. Following the R wave, the QRS complex is completed with an S wave that is generally characterized by a small positive inflection in the ECG signal. Following the S wave is a T-wave, which is separated from the S wave by the ST segment.

The data acquisition system 90 (or a separate similar system) can also convert analog signals received from the sensor (s) 14 into digital signals that can be monitored by a myocardial electrical stability detector 202 and/or a myocardial mechanical stability detector 204. Such signals can also be stored in memory 94.

The data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as an external programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

Also shown in FIG. 2 is the sensor 14 that is used to obtain a signal that is indicative of mechanical functioning of a patient's heart. As mentioned above, the sensor 14 can be: a pressure transducer that obtains measures of ventricular pressure; an accelerometer that obtains measures of contraction strength; a blood flow transducers that obtains measures of blood flow rate; an acoustic transducer that obtains measures of heart sounds; an impedance measuring circuit having voltage sense electrodes to measure volumetric alternans, which is a surrogate of mechanical alternans; a photo-plethysmography (PPG) sensor the measures pulse pressure; or a venous oxygen saturation (SVO2) sensor. Exemplary acoustic transducers are disclosed in U.S. Pat. No. 6,527,729 (Turcott), each of which is incorporated herein by reference. Exemplary implantable PPG sensors are disclosed in U.S. Pat. No. 6,409,675 (Turcott) and U.S. Pat. No. 6,731,967 (Turcott), and U.S. patent application Ser. No. 11/231,555 (Poore), filed Sep. 20, 2005, and Ser. No. 11/282,198 (Poore), filed Nov. 17, 2005, each of which is incorporated herein by reference. Exemplary pressure transducers are disclosed in U.S. patent application Ser. No. 11/072,942, filed Mar. 3, 2005 (Fayram et al.), which is incorporated herein by reference. These are just some examples of sensors that are capable of measuring the mechanical functioning of the heart, or a surrogate thereof. Other types of sensors capable of measuring the mechanical functioning of the heart, or a surrogate thereof, are also within the scope of the present invention.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external device 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 10, which provides operating power to a load that includes all of the circuits shown in FIG. 2.

Still referring to FIG. 2, in accordance with embodiments of the present invention, the microcontroller 60 includes a myocardial electrical stability detector 202, which as described in more detail below, can detect the presence of Twave alternans and/or other types of electrical alternans. The myocardial electrical stability detector 202 can be implemented within the microcontroller 60, as shown in FIG. 2. Thus, myocardial electrical stability detector 202 can be implemented by software, firmware, or combinations thereof. It is also possible that all, or portions, of the myocardial electrical stability detector 202 can be implemented using hardware. Further, it is possible that all, or portions, of the myocardial electrical stability detector 202 be implemented external to the microcontroller 60.

In an embodiment, the myocardial electrical stability detector 202 triggers data acquisition circuit 90 and timing control circuit 79 to record IEGM signal information. Using the IEGM signal information, myocardial electrical stability detector 202 can measure metrics of the signal (e.g., Twave metrics), such as Twave amplitude, Twave width, Twave slope, Twave area, Twave morphology, QT interval, evoked QT interval, etc. in the IEGM signal generated by the sensing circuits of the data acquisition system 90. Metrics of other portions of the IEGM signal, other than the Twave, can alternatively or additionally be measured.

Twave alternans have been demonstrated in many studies to be strong predictor of mortality, independent of left ventricular ejection fraction (LVEF). It had been generally believed that an elevated constant heart rate is a requirement for the detection of Twave alternans. However, a recent work published by Bullinga et al., entitled "Resonant Pacing Improves Twave Alternans Testing in Patients with Dilated Cardiomyopathy" (Heart Rhythm v1:S129, 2004) revealed a more robust detection with "resonant pacing" scheme. In this technique, Twave alternans with higher amplitudes were detected by pacing at a relatively shorter interval periodically once every fourth cycle during a moderately fast and constant pacing routine. This is an example of a patterned pacing sequence that repeats every 4 beats. Other examples of patterned pacing sequences are disclosed in U.S. patent application Ser. No. 10/884,276 (Bullinga), filed Jan. 6, 2005, (Publication No. US 2005/0004608), entitled "System and Method for Assessment of Cardiac Electrophysiologic Stability and Modulation of Cardiac Oscillations," which is incorporated herein by reference. Further examples of patterned pacing sequences are disclosed in U.S. patent application Ser. No. 11/341,086 (Farazi), filed Jan. 26, 2006, entitled "Pacing Schemes For Revealing Twave Alternans (TWA) at Low to Moderate Heart Rates," which is also incorporated herein by reference. The inventors of the present invention believe that such patterned pacing will also reveal mechanical alternans at lower heart rates. Instead of using patterned pacing, it is also believed that an intrinsic elevated heart rate or a paced elevated heart rate may also reveal Twave alternans and mechanical alternans.

Still referring to FIG. 2, in accordance with embodiments of the present invention, the microcontroller 60 includes a myocardial mechanical stability detector 204, which as described in more detail below, can monitor myocardial mechanical stability, e.g., by detecting the presence of mechanical alternans. The myocardial mechanical stability detector 204 can be implemented within the microcontroller 60, as shown in FIG. 2. Thus, myocardial mechanical stability detector 204 can be implemented by software, firmware, or combinations thereof. It is also possible that all, or portions, of the myocardial mechanical stability detector 204 can be implemented using hardware. Further, it is possible that all, or portions, of the myocardial mechanical stability detector 204 be implemented external to the microcontroller 60.

In an embodiment, the myocardial mechanical stability detector 204 triggers data acquisition circuit 90 and timing control circuit 79 to acquire a signal that is indicative of mechanical functioning of a patient's heart. Such a signal can be representative of an actual measure of mechanical functioning, or representative of a surrogate of mechanical functions. For an example, such a signal, if obtained from a pressure transducer within a ventricle, can be representative of ventricular pressure. In another embodiment, the signal is representative of contraction strength, which can be obtained from an accelerometer. In a further embodiment, the signal is representative of blood flow rate, which can be obtained from a blood flow transducer. In another embodiment, the signal is representative of heart sounds, which can be obtained from a microphone or an accelerometer that responds to acoustic vibrations transmitted through body fluids. In still another embodiment, the signal can representative of blood volume, which can be obtained using an impedance measuring circuit. In still another embodiment, the signal can be representative of pulse pressure, which can be obtained using a photoplethysmography sensor. In still another embodiment, the signal can be representative of venous oxygen saturation (SVO2). Each of the above elements are exemplary sensors that can be used to acquire a signal that is representative of mechanical functioning of a patient's heart, or a surrogate thereof. One of ordinary skill in the art, based on the disclosure herein, would understand that other types of sensors are also within the scope of the present invention.

Each of the above described signals are cyclical because they are indicative of the mechanical functioning of the heart, with each cycle of the signal corresponding to a beat of the patient's heart. The myocardial mechanical stability detector 204 can measure metrics of each cycle of the signal (i.e., metrics of each beat), to thereby determine whether there is an alternation in such metrics. Examples of such metrics include, but are not limited to, amplitude, width, area, and morphology. Depending on the signal being analyzed, the metrics can also be of specific portions or markers within the signal.

Also shown in FIG. 2 is a electro-mechanical stability detector 206, that can monitor a patient's myocardial electro-mechanical stability. In specific embodiments, the electro-mechanical stability detector 206 can determine a patient's risk of an adverse cardiac event based on both the patient's myocardial electrical stability and the patient's myocardial mechanical stability. Further, in specific embodiments, the electro-mechanical stability detector 206 can determine a myocardial electro-mechanical stability score (also referred to herein as a combined risk score), as explained in more detail below. Also, in specific embodiments, the electro-mechanical stability detector 206 can trigger a response that is specific to both the myocardial electrical stability and the myocardial mechanical stability, when the patient is at risk of an adverse cardiac event, as will be explained in more detail below. Additionally, in conjunction with the telemetry circuit 100, the myocardial electro-mechanical stability detector 206 can be configured to deliver status information, relating to the patient's myocardial stability, to the external device 102 through an established communication link 104. The myocardial electro-mechanical stability detector 206 can be implemented by software, firmware, hardware or combinations thereof. Further, it is possible that all, or portions, of the myocardial mechanical stability detector 204 be implemented external to the microcontroller 60.

Exemplary Programmer

Figure 3:
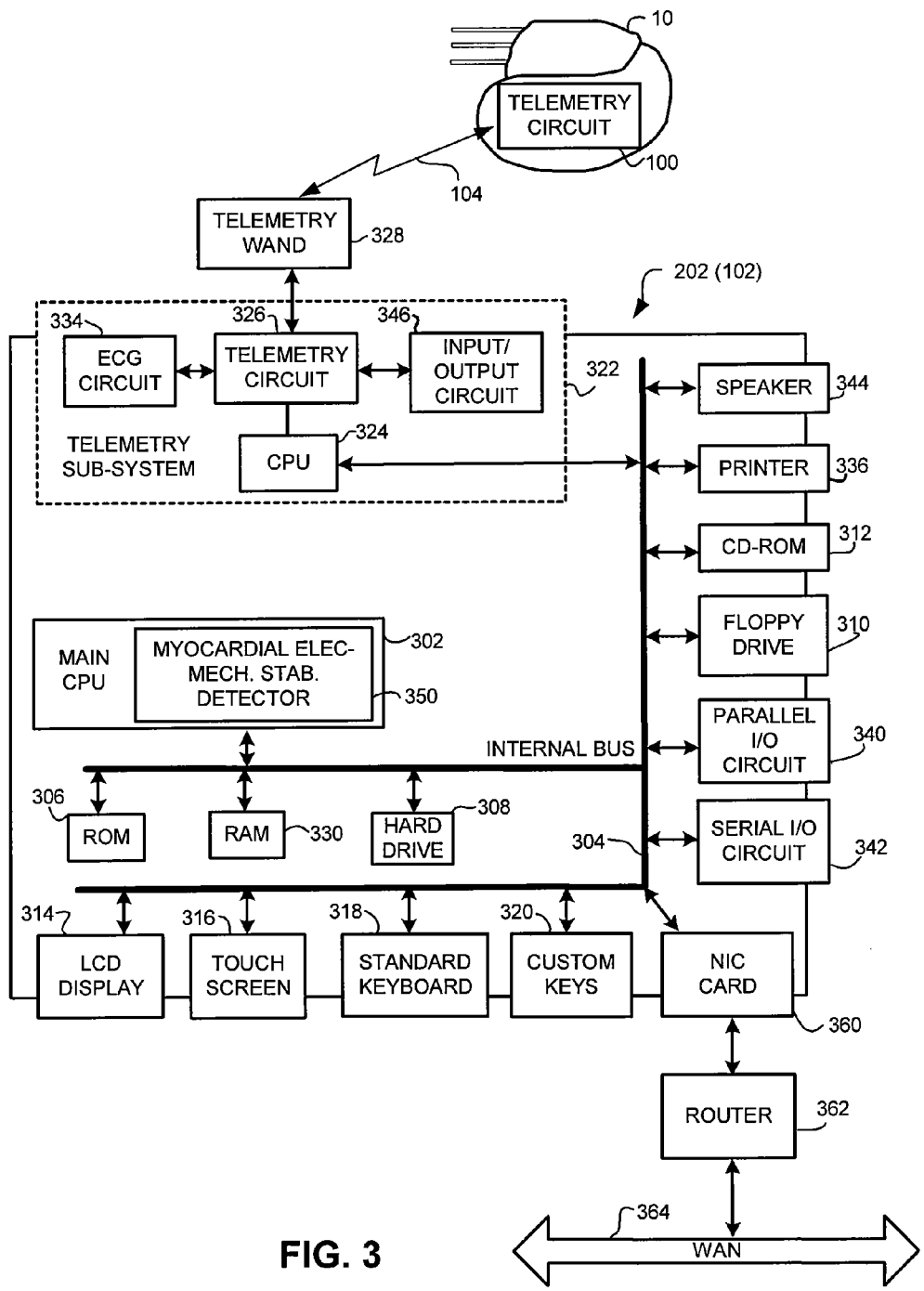
FIG. 3 is a functional block diagram illustrating components of an exemplary programmer for use with the implantable cardiac stimulation device of FIGS. 1 and 2.

FIG. 3 illustrates pertinent components of an exemplary programmer 202 for use in programming and communicating with an implantable cardiac stimulation device. The programmer 202 can also perform features of embodiments of the present invention, alone, or in combination with an implantable cardiac device (e.g., 10) with which it communicates. The programmer 202 is an example of the external device 102 introduced in FIG. 2. Briefly, the programmer 202 permits a physician or other authorized user to program the operation of the implantable cardiac stimulation device 10 and to retrieve and display information received from the implantable cardiac stimulation device 10 such as, IEGM data and device diagnostic data. Additionally, the programmer 202 may receive and display ECG data from separate external ECG leads that may be attached to the patient. Depending upon the specific programming of the programmer, programmer 202 may also be capable of processing and analyzing data received from the implantable cardiac stimulation device 10 and from ECG leads 332 to, for example, render preliminary diagnosis as to medical conditions of the patient or to the operations of the implantable cardiac stimulation device 10.

Now, considering the components of the programmer 202 by reference to FIG. 3, operations of the programmer 202 are controlled by a CPU 302, which may be a generally programmable microprocessor or microcontroller or may be a dedicated processing device such as an application specific integrated circuit (ASIC) or the like. Software instructions to be performed by the CPU can be accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 314 or other suitable computer display device. To this end, the CPU may, for example, display a menu of specific programming parameters of the implantable cardiac stimulation device 10 to be programmed or may display a menu of types of diagnostic data to be retrieved and displayed. In response thereto, the physician enters various commands via either a touch screen 316 overlaid on LCD display 314 or through a standard keyboard 318 supplemented by additional custom keys 320, such as an emergency VVI (EVVI) key. The EVVI key sets the implantable cardiac stimulation device 10 to a safe VI mode with high pacing outputs. This ensures life sustaining pacing operation in nearly all situations but by no means is it desirable to leave cardiac stimulation device 10 in the EVVI mode at all times.

Typically, the physician initially controls the programmer 202 to retrieve data stored within the implanted medical device and to also retrieve ECG data from ECG leads (examples discussed above with reference to FIGS. 1 and 2) coupled to the patient's myocardium. To this end, CPU 302 transmits appropriate signals to a telemetry circuit 322, which provides components for directly interfacing with implantable cardiac stimulation device 10. The telemetry subsystem 322 can includes its own separate CPU 324 for coordinating the operations of the telemetry subsystem 322. The main CPU 302 of the programmer 202 communicates with telemetry subsystem CPU 324 via internal bus 304. The telemetry subsystem 322 additionally includes a telemetry circuit 326 connected to a telemetry wand 328, which cooperate to receive and transmit signals electromagnetically from telemetry circuit 100 of the implantable cardiac stimulation device 10. The telemetry wand 328 is placed over the chest of the patient near the implanted cardiac stimulation device 10 to permit reliable transmission of data, over telemetric link 104, between the telemetry wand and the implantable cardiac stimulation device 10. Typically, at the beginning of the programming session, the external programming device controls the implantable cardiac stimulation device 10 via appropriate signals generated by telemetry wand 328 to output all previously recorded patient and device diagnostic information. Patient diagnostic information includes, for example, measured physiological variables data, recorded IEGM data and statistical patient data such as the percentage of paced versus sensed heartbeats. Device diagnostic data includes, for example, information representative of the operation of the implantable cardiac stimulation device 10 such as lead impedances, battery voltages, battery recommended replacement time (RRT) information and the like. Data retrieved from the implantable cardiac stimulation device 10 is stored by the external programmer 202 either within a random access memory (RAM) 330, a hard drive 308, within a floppy diskette placed within a floppy drive 310, etc. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implantable cardiac stimulation device 10 is transferred to the programmer 202, the implantable cardiac stimulation device 10 may be further controlled perform an electrode setup algorithm of the present invention, which are described in more detail below.

The programmer 202 can also include a network interface card ("NIC") 360 to permit transmission of data to and from other computer systems via a router 362 and wide area network ("WAN") 364. Alternatively, the programmer 202 might include a modem (not shown) for communication via the public switched telephone network (PSTN). Depending upon the implementation, the modem may be connected directly to internal bus 304 may be connected to the internal bus via either a parallel port 340 or a serial port 342. Data transmitted from other computer systems may include, for example, data regarding medication prescribed, administered or sold to the patient.

The CPU 302 can include a myocardial electro-mechanical stability detector 350 that can monitor a patient's myocardial electro-mechanical stability based on signals receive from the implantable device 10, or based on signals it receives from external sensors and electrodes. The detector 350 can determine a patient's risk of an adverse cardiac event based on both a patient's myocardial electrical stability and a patient's myocardial mechanical stability, which can be determined by blocks 202 and 204 of the implantable device, or within the programmer 202. In a similar manner as block 206, detector 350 can determine a myocardial electro-mechanical stability score (also referred to herein as a combined risk score), as well as trigger a response that is specific to both the myocardial electrical stability and the myocardial mechanical stability. It is also possible that detector 350 can be implemented by software, firmware, hardware or combinations thereof.

The programmer 202 can receive signal from the implantable cardiac stimulation device 10, including signal(s) indicative of electrical functioning of the patient's heart and/or signal(s) indicative of mechanical functioning of the patient's heart. Additional, or alternatively, the programmer 202 can receive ECG signals from separate external ECG leads, or signal representative of oxygen saturation from a finger or earclip type pulse oxymeter, or other signals from other types of non-implanted sensors. The external programmer 202 can also display to a physician a patient's myocardial electrical stability and myocardial mechanical stability and a combined risk score. The programmer 202 can also trigger various alerts, depending on such stabilities and/or score. Any or all of the information displayed by programmer 202 may also be printed using a printer 336.

A speaker 344 is included for providing audible tones to the user, such as a warning beep in the event improper input is provided by the physician. Telemetry subsystem 322 may additionally include an input/output circuit 346 which can control the transmission of analog output signals, such as ECG signals output to an ECG machine or chart recorder. Other peripheral devices may be connected to the external programmer 202 via parallel port 340 or a serial port 342 as well. Although one of each is shown, a plurality of input output (10) ports might be provided.

With the programmer 202 configured as shown, a physician or other authorized user can retrieve, process and display a wide range of information received from the implantable cardiac stimulation device 10 and reprogram the implantable cardiac stimulation device 10 if needed. The descriptions provided herein with respect to FIG. 3 are intended merely to provide an overview of the operation of the exemplary programmer 202 and are not intended to describe in detail every feature of the hardware and software of the device and are not intended to provide an exhaustive list of the functions performed by the device.

Flow Charts

Figure 4:
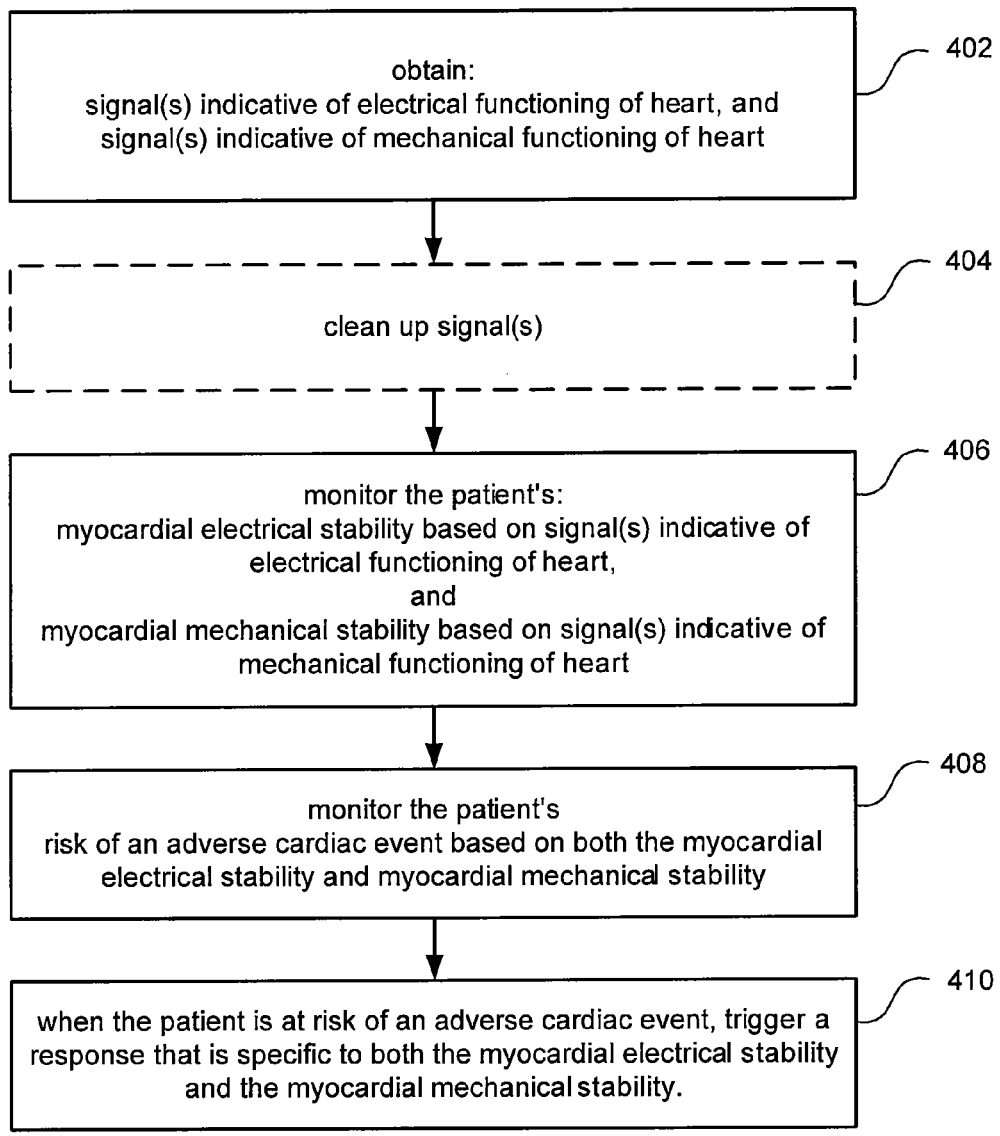
FIG. 4 is a high-level flow diagram that is useful for describing embodiments of the present invention that are used to monitor and respond to myocardial electro-mechanical stability.
Figure 5:
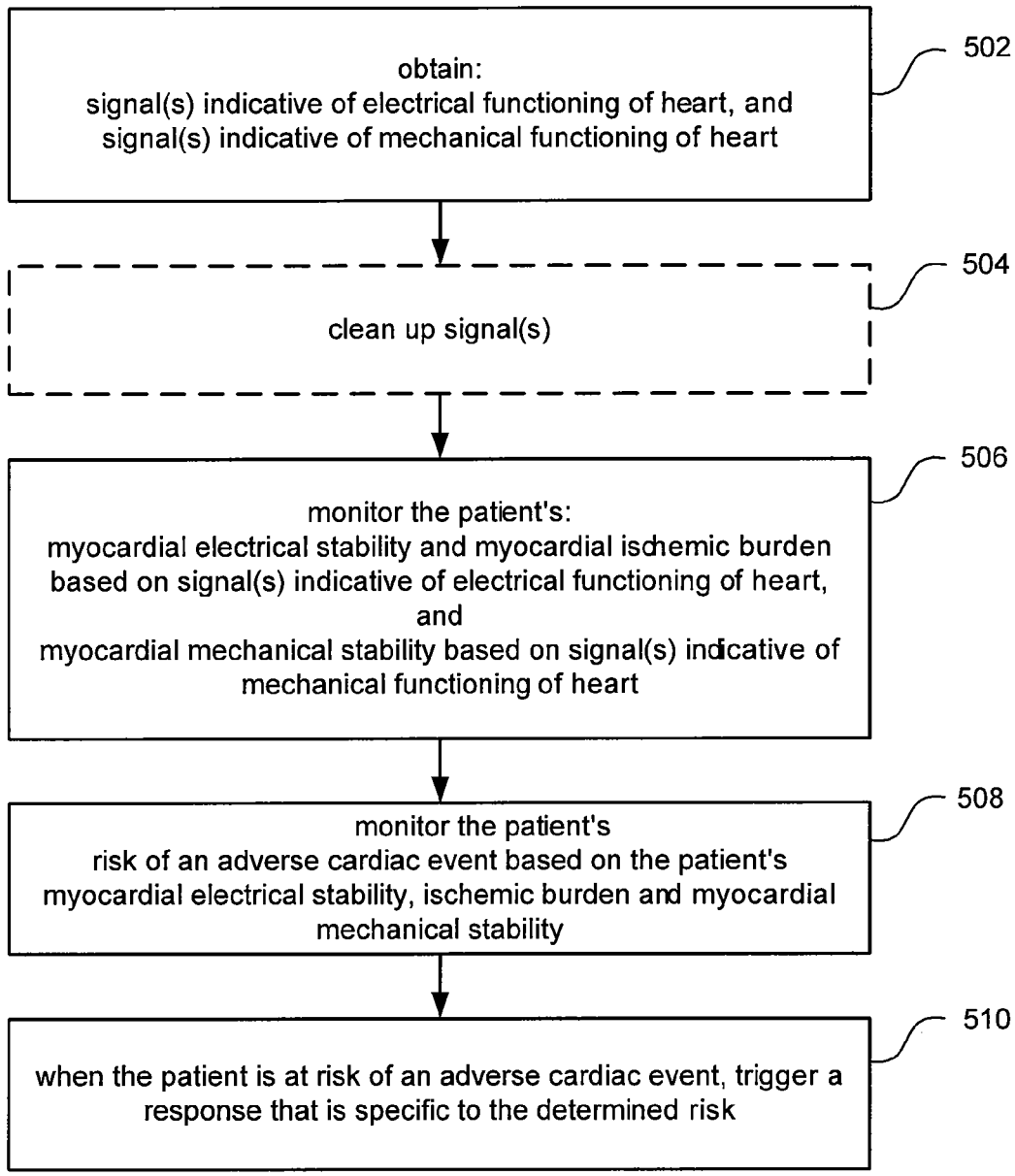
FIG. 5 is a high-level flow diagram that is useful for describing additional embodiments of the present invention.

Specific embodiments of the present invention will now be summarized with reference to the high level flow diagrams of FIGS. 4 and 5. In the flow diagrams described herein, the various algorithmic steps are summarized in individual "blocks". Such blocks describe specific actions or decisions that are made or carried out as the algorithm proceeds. Where one or more microcontroller (or equivalent) is employed, the flow diagrams presented herein provide the basis for a "control program" that may be used by such a microcontroller (or equivalent) to effectuate the desired control of the cardiac device. Those skilled in the art may readily write such a control program based on the flow diagrams and other descriptions presented herein. The steps of the flow diagrams can be implemented, e.g., by an implantable cardiac device, such as but not limited to the ICD 10, by an external device, such as programmer 202, or combinations thereof. In other words, in certain embodiments, all or most of the steps are performed within an implanted cardiac device (e.g., 10). In other embodiments, all or most of the steps are performed in a non-implanted device, such as an external programmer (e.g., 202). In further embodiments, some (or portions) of the steps are performed within an implanted cardiac device, and others (or portions) are performed within an external device, which are in communication with one another.

Referring to FIG. 4, at a step 402 one or more signal indicative of electrical functioning of a patient's heart is obtained, as is one or more further signal indicative of mechanical functioning of the patient's heart.

In accordance with a preferred embodiment, the one or more signal indicative of electrical functioning of the patient's heart includes an intra cardiac electrogram (IEGM) signal obtained using leads placed within or in close proximity to the patient's heart. Exemplary leads 20, 24 and 30 were discussed above with reference to FIG. 1, and exemplary electrodes connected to such leads were discussed above with reference to FIGS. 1 and 2. Its also possible that the one or more signal indicative of electrical functioning of the patient's heart includes an ECG signal obtained using external ECG leads.

A signal indicative of mechanical function of the patient's heart can be an actual measure of mechanical functioning, or representative of a surrogate of mechanical functions. In accordance with an embodiment, this signal is representative of ventricular pressure, and is obtained from a pressure transducer within a ventricle. In another embodiment, this signal is representative of contraction strength and is obtained from an accelerometer. In a further embodiment, this signal is representative of blood flow rate and is obtained from a blood flow transducer. In another embodiment, this signal is representative of heart sounds and is obtained from a microphone or an accelerometer that responds to acoustic vibrations transmitted through body fluids. In still another embodiment, this signal is representative of blood volume and is obtained using an impedance measuring circuit. In still another embodiment, this signal is representative of pulse pressure and is obtained using a photo-plethysmography sensor. In another embodiment, this signal is representative of venous oxygen saturation and is obtained using an SVO2 sensor. The above mentioned elements are exemplary sensors that can be used to acquire a signal that is indicative of mechanical functioning of a patient's heart. One of ordinary skill in the art, based on the disclosure herein, would understand that other types signals obtained from other types of sensors are also within the scope of the present invention. In accordance with an embodiment, data indicative of the signal(s) is/are stored within the ICD 10 (e.g., in memory 94). While some of the above discussed signals can only be obtained by implanted sensors, other can be obtained using implanted or non-implanted (e.g., ambulatory) sensors.

At an optional step 404, one or more signal obtained at step 402 is/are cleaned up. This can be accomplished, e.g., by filtering a signal (or data indicative of the signal) and/or removing noisy cycle segments of a signal. Filtering a signal could include, e.g., the use of a low-pass filter with a cutoff frequency of about 250 Hz. Additionally, a high-pass filter can be used to reduce the contribution of DC-offsets and respiration drift to a signal. Removal of noisy cycles can be accomplished, e.g., by removing any number of cycles that are exposed to severe noise, e.g., from myopotentials or electromagnetic interference. A further optional step is to resample stored cycles of a signal to match in length. For example, if a signal were originally sampled at 256 Hz, it could be upsampled to 1000 Hz, stretched or compressed to match a mean cycle length, and then down-sampled again to 256 Hz. Additional details of how this can be done are provide in commonly assigned U.S. patent Ser. No. 11/561,259, entitled "Systems and Methods for Detecting Alternans in Intrinsic Rhythms to Monitor Myocardial Stability" (Farazi), filed Nov. 17, 2006, which is incorporated herein by reference. The above described pre-processing to clean up the signal generally helps to minimize noise in the signal. Step 404 can also include removing easily detected ectopic beats (e.g., premature contractions of the ventricles). For example, this can be accomplished by comparing each cardiac length to a mean cardiac length. An ectopic beat can then be identified where a length of a beat is less than a threshold percentage (e.g., 80%) of the mean length, yet is surrounded by beats having lengths that are greater than the threshold percentage.

At a step 406, the patient's myocardial electrical stability is monitored based on the one or more signal indicative of electrical functioning of the patient's heart, and the patient's myocardial mechanical stability is monitored based on the one or more signal indicative of mechanical functioning of the patient's heart. In accordance with specific embodiments, step 406 is accomplished by monitoring a degree of electrical alternans based on the one or more signal indicative of electrical functioning of the patient's heart, and monitoring a degree of mechanical alternans based on the one or more signal indicative of mechanical functioning of the patient's heart. In certain embodiments, the degree of alternans can simply be whether or not alternans beyond a threshold exist, or more granular degrees of alternans can be determined. Additional details of how to monitor for myocardial electrical and mechanical stability, including how to monitor for electrical and mechanical alternans are discussed below.

At a step 408, the patient's risk of an adverse cardiac event is monitored based on both the myocardial electrical stability and myocardial mechanical stability. Such an adverse cardiac event can be, but is not limited to, an arrhythmia, sudden cardiac death (SCD), a myocardial infarction, or an acute heart failure exacerbation. Where step 406 is accomplished by monitoring a degree of electrical alternans based on the one or more signal indicative of electrical functioning of the patient's heart, and monitoring a degree of mechanical alternans based on the one or more signal indicative of mechanical functioning of the patient's heart, then step 408 can include monitoring the patient's risk of an adverse cardiac event based on the monitored degrees of electrical and mechanical alternans. As explained in more detail below, step 408 can include determining a combined risk score indicative of the patient's risk of an adverse cardiac event.

At a step 410, when the patient is at risk of an adverse cardiac event, a response is triggered that is specific to both the myocardial electrical stability and the myocardial mechanical stability of the patient. For example, step 410 can include triggering a response that is specific to both a degree of electrical alternans and a degree of mechanical alternans. This can include selecting from at least two different responses when the patient is at risk of an adverse cardiac event. In specific embodiments, the responses involve delivering types of cardiac therapy. Alternatively, or additionally, the responses can involve notifying types of cardiac specialists or other caregivers.

In accordance with an embodiment, step 410 includes triggering a first response if electrical alternans are present but mechanical alternans are not present, triggering a second response (that is different from the first response), if mechanical alternans are present but electrical alternans are not present, and triggering a third response if both electrical and mechanical alternans are present. The first, second and third responses can involve, e.g., delivering types of cardiac therapy, stimulating vagal nerves and/or notifying types of cardiac specialists. Additional details of types of responses are discussed below.

As mentioned above, step 406 can include monitoring a degree of electrical alternans based on the one or more signal indicative of electrical functioning of the patient's heart, and monitoring a degree of mechanical alternans based on the one or more signal indicative of mechanical functioning of the patient's heart, to monitor, respectively, the patient's myocardial electrical stability and myocardial mechanical stability. Additional details of how step 406 can be performed are now provided.

In accordance with specific embodiments, to monitor myocardial electrical stability, T-wave metrics can be measured to determined whether alternations in T-waves exist, and to what extent. Below are some example of how T-wave alternans can be detected. However, it is noted that embodiments of the present invention should not be limited to the specific techniques described.

The term T-wave as used herein may refer to a portion of the ventricular QRS-T-wave complex of an IEGM or ECG that includes the T-wave and/or the QRS-T segment. The alternating feature of Twave alternans can be detected by examination, for example, of the QT interval, T-wave width, T-wave amplitude, morphology, etc. Whatever the designated portion of the intracardiac electrogram, electrical alternans refers to an alternating pattern of the wave that can be designated "ABABAB . . . " where A represents every other cycle and B represents every other alternate cycle. Such a pattern is often referred to as a two beat alternans pattern, or simply an AB pattern. Electrical alternans may also refer to an alternating pattern of the wave that can be designated "ABCABC . . . ", or an alternating pattern of the wave that can be designated "ABCDABCD . . . ". The "ABCABC . . . " pattern is a three beat alternans pattern, which can be simply referred to as an ABC pattern, and the "ABCDABCD . . . " pattern is a four beat alternans pattern, which can be referred to as an ABCD pattern.

One way to detect the presence of an AB alternans pattern is to measure T-wave metrics for a plurality of consecutive beats represented in the adjusted sample data resulting from step 404, and then line up all the T-wave metrics of odd beats, and line up all the T-wave metrics of even beats. Ensemble averaging (or some other averaging) can then be performed to produce one or more average "odd" T-wave metric and one or more average "even" T-wave metric. A magnitude of alternation can then be determined by determining a difference between an average "odd" T-wave metric and a corresponding average "even" T-wave metric. This difference (i.e., magnitude of alternation) can be compared to a threshold to determine if T-wave alternans are present. If the difference is less than the threshold, then it can be determined that T-wave alternans are not present. If the difference (i.e., the magnitude of alternation) is greater than the threshold, then it can be determined that the T-wave alternans are present. It is also possible to have multiple thresholds such that in addition to determining whether T-wave alternans are present, changes in magnitudes of alternations can be determined. This can be used, e.g., to determine a degree of the T-wave alternans, which are indicative of degrees of myocardial electrical stability. This can also be used for tracking the progression of a disease that influences the electrical stability of the myocardium. Additionally, a degree of the T-wave alternans (or more generally, magnitudes of alternation) can be used as an index of the level of risk for an impending ventricular arrhythmia. This type of algorithm can also be modified to look for other (e.g., three of four beat) alternans patterns.

Alternatively, the variation in T-wave amplitude of successive "odd" T-waves and "even" T-waves can be measured in a sliding window. The amount of T-wave variation between the odd and even T-waves can be determined. A third measure that determines the statistical significance of the difference in T-wave variations as compared to a baseline can be used to determine the presence, degree, or absence of T-wave alternans, and thus, the electrical stability of the myocardium.

Another option would be to determine, for each pair of odd/even beats, the difference between T-wave amplitudes of the odd and even beats. Assuming such differences (which are examples of magnitudes of alternation) are determined for each of 50 separate pairs of beats, then the differences of the 50 pairs can be averaged to produce an average difference, and the presence of T-wave alternans can then be determined from the average difference.

As mentioned above, not all alternans patterns are two beat patterns. Rather, there can be three beat, four beat, etc. alternans patterns. For example, a four beat alternans (ABCD) pattern can be searched for in the following manner. Assume that 200 consecutive beats are divided into 50 separate 4 beat sets. For each 4 beat set, there can be a determination of the difference between T-wave amplitudes of the 1st and 2nd beats, the 2nd and 3rd beats, and the 3rd and 4th beats, resulting in three differences for each 4 beat set (i.e., a first difference between the metrics for 1st and 2nd beats, a second difference between the metrics for the 2nd and 3rd beats, and a third difference between the metrics for the 3rd and 4th beats). Assuming such differences (which are examples of magnitudes of alternation) are determined for each of 50 separate 4 beat sets, then the first difference of each of the 50 sets can be averaged to produce an average first difference, the second difference of each of the 50 sets can be averaged to produce an average second difference, and the third difference of each of the 50 sets can be average to produce an average third difference. The presence of T-wave alternans can then be determined from the average first difference, the average second difference and the average third difference.

Further algorithms rely of frequency domain analysis for detecting electrical alternans. Exemplary systems and methods for detecting electrical alternans, and more generally, monitoring myocardial electrical stability, are provided in the following commonly assigned applications, which are both incorporated herein by reference: U.S. patent application Ser. No. 11/354,699, entitled "Time Domain Monitoring of Myocardial Electrical Stability," and U.S. patent application Ser. No. 11/354,732, entitled "Frequency Domain Monitoring of Myocardial Electrical Stability," both of which were filed Feb. 14, 2006.

These are just a few examples of the ways in which the presence of electrical alternans can be detected, or more generally, that myocardial electrical stability can be monitored, at step 406. One of ordinary skill in the art will appreciate that many other different techniques can be used, while still being within the spirit and scope of the present invention.

Techniques for detecting mechanical alternans in a signal representative of mechanical functioning of a patient's heart are similar to those that are used for detecting electrical alternans in a signal representative of electrical functioning of a patient's heart. The difference is the signal being analyzed, and the metric(s) of the signal being measured. Exemplary signals that are indicative of mechanical functioning of a patient's heart are provided above. The metric(s) of such signals that can be determined for each of a plurality of consecutive beats can be, e.g., maximum amplitude, peak-to-peak amplitude, width, area, morphology, or the like. Further exemplary systems and methods for detecting mechanical alternans, and more generally, monitoring myocardial mechanical stability, are provided in commonly assigned U.S. patent application Ser. No. 11/421,915, filed Jun. 2, 2006, entitled "Methods and Devices for Monitoring Myocardial Mechanical Stability,".

If at step 406 it is determined that electrical alternans are present, there may be a determination at step 408 that the patient has a heightened risk of an arrhythmia. If at step 406 it is determined that mechanical alternans are present, there may be a determination at step 408 that the patient has a heightened risk of an acute heart failure exacerbation. If at step 406, it is determined that both electrical and mechanical alternans are present, there may be a determination at step 408 that the patient has a heightened risk of both a ventricular arrhythmia and an acute heart failure exacerbation.

As mentioned above, at step 410, a response is triggered that is specific to both the myocardial electrical stability and the myocardial mechanical stability, when a patient is at risk of an adverse cardiac event. For example, a first response can be triggered if electrical alternans are present but mechanical alternans are not present, a second response (that is different from the first response) can be triggered if mechanical alternans are present but electrical alternans are not present, and a third response can be triggered if both electrical and mechanical alternans are present. The third response may be different than both the first and second responses, the same as one of the first and second responses, or a combination of the first and second responses, depending upon how the ICD is programmed by a physician. Preferably the responses are such that treating mechanical instability does not adversely affect electrical stability and vice versa. It is also within the scope of the present invention that degrees of instability be determined so that the more instable one of electrical and mechanical stability be treated first. For example, a treatment specific to treating electrical instability may be provided before a treatment for mechanical instability, if the patient's myocardium is more electrically instable than mechanically instable.

If is determined at steps 406 and 408 that electrical alternans are present and that the patient has a heightened risk of an arrhythmic events (such as a tachyarrhythmia, and more specifically a ventricular arrhythmia), then arrhythmia prevention therapy can be triggered at step 410. One type of therapy would be for an implanted device (e.g., device 10) to stimulate the patient's vagus nerve, in an attempt to prevent an arrhythmia from occurring. In another embodiment, the implanted device, if appropriately equipped, can deliver appropriate anti-arrhythmia drug therapy. In still another embodiment, the implanted device, if appropriately equipped, can deliver appropriate pacing therapy, including, but not limited to, resynchronization therapy. In still another embodiment, the implantable device, if capable of delivering shock therapy, can begin to charge its capacitors in case the patient goes into ventricular fibrillation and needs shock therapy. These are just a few examples of the types of responses that can be performed upon detection of a heightened risk of an arrhythmia. One of ordinary skill in the art would understand from the above description that other response are also possible, while still being within the spirit and scope of the present invention.

If it is determined at steps 406 and 408 that mechanical alternans are present and that the patient has a heightened risk of an acute heart failure exacerbation, then at step 410 an appropriate therapy can be triggered. One type of therapy would be for an implanted device, if appropriately equipped, to deliver appropriate drug therapy. In another embodiment, the implantable device can perform appropriate pacing therapy to treat an acute heart failure exacerbation. One of ordinary skill in the art would understand from the above description that other responses are also possible, while still being within the spirit and scope of the present invention.

Additionally or alternatively, a patient can be alerted (e.g., using alert 118) at step 410 if e.g., at step 408 there is a detection of a heightened risk of an arrhythmia and/or a heightened risk of an acute heart failure exacerbation. The same alert can be used for each type of detected heightened risk, or the alert can be specific to the type of risk. For example, a first type of alert can be triggered if it is determined that the patient is at a heightened risk of an arrhythmia and a second type of alert (distinguishable from the first type of alert) can be triggered if it is determined that the patient is at a heightened risk of an acute heart failure exacerbation. A third type of alert can be triggered if the patient is both at a heightened risk of an arrhythmia and at a heightened risk of an acute heart failure exacerbation. The third type of alert can be different than the other two types of alerts, or a combination thereof.

An alert could be a vibratory or auditory alert that originates from within the implantable device 10. Alternatively, the implantable device 10 may wirelessly transmit an alert to an external device (e.g., 102) that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible an arrhythmia may be avoided, or if it does occur, the patient will be less dangerous to themselves and others if the patient is resting when the arrhythmia occurs (as opposed, e.g., to driving a car). It is also possible that an external device (e.g., 102/202) can generate the alert.

Additionally or alternatively, the patient can be instructed to take medication when alerted. For example, a patient can be instructed to take a first type of medication if it is determined that the patient is at a heightened risk of an arrhythmia, and instructed to take a second type of medication if it is determined that the patient is at a heightened risk of an acute heart failure exacerbation. The patient can be triggered to take a third type of medication, both the first and second types of medications, or one of the first and second types of medication, if it is determined that the patient is both at a heightened risk of an arrhythmia and at a heightened risk of an acute heart failure exacerbation.

Additionally or alternatively, a first caregiver (e.g., physician) can be alerted if it is determined that the patient is at a heightened risk of an arrhythmia, and a second caregiver can be alerted if it is determined that the patient is at a heightened risk of an acute heart failure exacerbation. If it is determined that the patient is both at a heightened risk of an arrhythmia and at a heightened risk of an acute heart failure exacerbation, then a third caregiver can be alerted, and/or the first and/or second caregiver can be alerted. This way, the correct caregiver can contact the patient to check on the patient's status, and/or request that the patient visit the caregiver's office. Also, if the patient is in a care facility (e.g., a hospital), the appropriate caregiver can be immediately dispatched to the patient. The different types of caregivers can be, e.g., different types of cardiac specialists. For example, an electro-physiologist can be alerted if it is determined that the patient has a heightened risk of an arrhythmia, and a heart failure specialist can be alerted if the patient has a heightened risk of an acute heart failure exacerbation.

Additionally or alternatively, information related to the electrical alternans and mechanical alternans can be stored. This can include, for example, storing amplitude, slope, timing, and/or duration information relating to the alternans. If such information is stored in an implanted device, such information can be continually, or from time to time, automatically uploaded to an external device (e.g., 102). Such an external device 102 can be located, e.g., in the patient's home, and the information can be transmitted (e.g., through telephone lines or the Internet) to a medical facility where a physician can analyze the information. For example, the external device 102 can be a bedside monitor, or an ambulatory device that the patient carries with them. Alternatively, the external device can be an external programmer located at a medical facility, and the information can be uploaded when the patient visits the facility.

In further embodiments, changes in myocardial electrical and mechanical stability are tracked, as described above. One or more of the above described responses occur if the electrical instability of the myocardium exceeds a corresponding threshold, or electrical stability of the myocardium falls below a corresponding threshold. Similarly, one or more of the above described responses occur if the mechanical instability of the myocardium exceeds a corresponding threshold, or mechanical stability of the myocardium falls below a corresponding threshold. In a specific embodiment, magnitudes of alternans are tracked over time to thereby track how a patient's myocardial electro-mechanical stability changes over time. For example, a patient may be paced for a period of time, once per day (or week, or month or other period) using the same patterned pacing sequence (or elevated pacing rate) intended to invoke alternans, and a magnitude of electrical and mechanical alternans can be determined each time. It's also possible to measure degrees of electrical and mechanical alternans whenever an intrinsic heart rate exceeds a threshold rate which is likely to reveal such alternans, should they exist. If over time the magnitudes of electrical alternans increase, it can be determined that the patient's myocardial electrical stability is worsening; and if over time the magnitudes of electrical alternans decrease, it can be determined that the patient's myocardial electrical stability is improving. Similarly, if over time the magnitudes of mechanical alternans increase, it can be determined that the patient's myocardial mechanical stability is worsening; and if over time the magnitudes of mechanical alternans decrease, it can be determined that the patient's myocardial mechanical stability is improving. If over time the magnitudes of electrical and mechanical alternans increase, it can be determined that the patient's myocardial electro-mechanical stability is worsening; and if over time the magnitudes of electrical and mechanical alternans decrease, it can be determined that the patient's myocardial electro-mechanical stability is improving. It is also possible that electrical stability may worsen while mechanical stability improves, or vice versa.

In accordance with specific embodiments, at step 406 a degree of electrical alternans and degree of mechanical alternans are determined and stored. A predefined criterion can be programmed in the ICD (e.g., 10) that translates the raw values of each type of alternans to a risk index. For example, an algorithm can be used to translate the degree of electrical alternans (e.g., T-wave alternans) to an index of electrical stability. Similarly, the degree of mechanical alternans can also translated to an index of mechanical stability. In accordance with an embodiment, using predefined thresholds, a 2×2 matrix is created and used to produce a combined risk score, which is also referred to as a myocardial electro-mechanical stability score.

In certain embodiments, myocardial electrical stability and myocardial mechanical stability are assumed to have independent mechanisms, and the combined score can be determined, e.g., by adding each risk index. For a simple example, the presence of electrical alternans beyond a corresponding threshold adds one to the risk index, where zero is added to the risk index if the threshold is not exceeded. Similarly, the presence of mechanical alternans beyond a corresponding threshold adds one to the risk index, where zero is added to the risk index if the threshold is not exceeded. Thus, in this example, a resulting myocardial electro-mechanical stability score (i.e., the combined risk score) can have a value of 0, 1, 2 or 3. Levels of alternation need not have just two levels, but rather, there can be further levels of granularity, which will provide the risk index with further levels of granularity. For example, if three degrees of electrical alternation and three degrees of mechanical alternation can be determined, e.g., by using two electrical alternation thresholds and two mechanical alternation thresholds, then there can be six levels of risk in a risk index (e.g., from 0 to 5). It is also possible that degrees of electrical alternans are weighted differently than degrees of mechanical alternans, when determining a combined risk score. For example, the presence of electrical alternans may be weighted twice as much as the presence of mechanical alternans, or vice versa.

In certain embodiments, myocardial electrical stability and myocardial mechanical stability are assumed to have dependent underlying mechanisms, and the combined risk score is produced using a function other than addition, e.g., by using weighting factors, or the like. For a more specific example, the presence of electrical alternans beyond a corresponding threshold without mechanical alternans beyond a corresponding threshold, or vice versa, may result in a risk score of 2, whereas if there were both electrical and mechanical alternans beyond their corresponding thresholds, the risk index score may only be increased to 3.

In specific embodiments, the two risk indices can be used to define a two dimensional space representative of electro-mechanical stability with less defined boundaries. This can be accomplished, e.g., by not using thresholds, but rather assuming any magnitude of electrical alternation and mechanical alternation is indicative of risk. Magnitudes of alternation can then be added or otherwise combined to determine a risk score. For example, if a magnitude of electrical alternation is 3.3 and a magnitude of mechanical alternation is 1.5, then a combined risk score can simply be determined by adding 3.3 and 1.5, to get 4.8. It is also possible that weighting factors and/or normalization factors be used.

In another embodiment, a third dimension of risk may be added to the matrix used to determine a combined risk score. For example, the third dimension can be an assessment of myocardial ischemic burden. The index of risk as indicated by an ischemic burden assessment may not be mutually exclusive of the other risk indices. For example, an increased level of ischemic burden may affect the electrical stability of the myocardium and as such can be used to adjust the thresholds used in the electrical stability dimension and/or used to calculate a combined score for risk of adverse cardiac events. In addition, this information can be used for redirecting therapy (e.g., device therapy or medication) and/or differentially notifying medical specialists. The combined electro-mechanical risk score derived by this method can be used to predict SCD in the setting of HF. Presence or absence of ischemia will also affect this decision since an increase in ischemia burden directly decreases the electrical stability of the heart. For example, if electrical alternans beyond a threshold are detected, but there is no ischemic burden beyond a threshold, this may result in a lower risk score than if both electrical alternans and ischemic burden exceeded corresponding thresholds.

Myocardial ischemic events can be monitored by detecting an acute voltage shift in the ST-segment of an IEGM. Ischemic burden can then be monitored, e.g., by determining a number of ischemic events that occur during each predetermined period (e.g., 24 hours). Other exemplary techniques for detecting ischemic events, and for monitoring ischemic burden are provided in U.S. patent application Ser. No. 11/557,814, entitled "Implantable Devices, and Methods for Use therewith, for Monitoring Sympathetic and Parasympathetic Influences on the Heart", filed Nov. 8, 2006, which is incorporated herein by reference.

The high level flow diagram of FIG. 5, which includes steps 502-510, summarizes one way in which myocardial ischemic burden can also be used when determining a patient's risk of an adverse cardiac event. For example, it may be determined that the patient is at their lowest risk when electrical alternans, mechanical alternans and ischemic burden do not exceed their corresponding thresholds. Conversely, it may be determined that the patient is at their highest risk when electrical alternans, mechanical alternans and ischemic burden all exceed their corresponding thresholds.

In alternative embodiments, ischemic burden can be continually or periodically monitored, and there can be a check for electro-mechanical stability only when ischemic burden passes a certain threshold or increases by certain percentage over its baseline value. In other embodiments, myocardial electro-mechanical stability is continually or periodically monitored, and when electro-mechanical stability drops below a threshold (or electro-mechanical instability exceeds a threshold), then the ICD can begin to monitor for myocardial ischemic events, or if it was already monitoring for myocardial ischemic events, can determine the patient's ischemic burden. In still other embodiments, the ICD periodically determines the patient's electro-mechanical stability and ischemic burden.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. A method comprising:
   (a) obtaining one or more signals indicative of electrical functioning of a patient's heart, and one or more signals indicative of mechanical functioning of the patient's heart;
   (b) determining the patient's myocardial electrical stability by determining a degree of electrical alternans based on the one or more signals indicative of electrical functioning of the patient's heart, and determining the patient's myocardial mechanical stability by determining at least three degrees of mechanical alternans using a plurality of thresholds based on the one or more signals indicative of mechanical functioning of the patient's heart;
   (c) determining a myocardial electro-mechanical stability score based on the patient's myocardial electrical stability and myocardial mechanical stability;
   (d) determining whether the patient is at risk of an adverse cardiac event based on the myocardial electro-mechanical stability score;
   (e) when the patient is at risk of an adverse cardiac event, triggering a response that is specific to both the myocardial electrical stability and the myocardial mechanical stability of the patient;
   (f) using an algorithm to determine whether the patient's myocardium is more electrically unstable or mechanically unstable;
   (g) if the patient's myocardium is more electrically unstable than mechanically unstable, treating the electrical instability first, wherein treating the electrical instability first comprises using a treatment specific to the electrical instability before using a treatment specific to the mechanical instability; and
   (h) if the patient's myocardium is less electrically unstable than mechanically unstable, treating the mechanical instability first, wherein treating the mechanical instability first comprises using a treatment specific to the mechanical instability before using a treatment specific to the electrical instability.

2. The method of claim 1, wherein step (c) includes using an algorithm to determine the myocardial electro-mechanical stability score, where the algorithm treats myocardial electrical stability and myocardial mechanical stability as being independent risk factors.

3. The method of claim 1, wherein step (c) includes using an algorithm to determine the myocardial electro-mechanical stability score, where the algorithm treats myocardial electrical stability and myocardial mechanical stability as being dependent risk factors.

4. The method of claim 1, further comprising determining the patient's myocardial ischemic burden; and wherein step (c) comprises determining the myocardial electro-mechanical stability score also based on the patient's myocardial ischemic burden.

5. The method of claim 1, wherein step (e) comprises triggering a response that is specific to both the degree of electrical alternans and the degree of mechanical alternans.

6. The method of claim 5, wherein triggering a response that is specific to both the degree of electrical alternans and the degree of mechanical alternans comprises selecting from at least two different responses when the patient is at risk of an adverse cardiac event.

7. The method of claim 5, wherein the responses comprise delivering types of cardiac therapy.

8. The method of claim 5, wherein the responses comprise notifying types of cardiac specialists or other caregivers.

9. A non-transitory computer readable medium having instructions that when executed on a processor of an implantable medical device (IMD) having cardiac pacing capabilities cause the IMD to:
(a) obtain one or more signals indicative of electrical functioning of a patient's heart, and one or more signals indicative of mechanical functioning of the patient's heart;
(b) determine the patient's myocardial electrical stability by determining a degree of electrical alternans based on the one or more signals indicative of electrical functioning of the patient's heart, and determine the patient's myocardial mechanical stability by determining at least three degrees of mechanical alternans using a plurality of thresholds based on the one or more signals indicative of mechanical functioning of the patient's heart;
(c) determine a myocardial electro-mechanical stability score based on the patient's myocardial electrical stability and myocardial mechanical stability;
(d) determine whether the patient is at risk of an adverse cardiac event based on the myocardial electro-mechanical stability score;
(e) when the patient is at risk of an adverse cardiac event, trigger a response that is specific to both the myocardial electrical stability and the myocardial mechanical stability of the patient, wherein the IMD uses an algorithm to determine whether the patient's myocardium is more electrically unstable or mechanically unstable;
(g) if the patient's myocardium is more electrically unstable than mechanically unstable, treat the electrical instability first, wherein treating the electrical instability first comprises using a treatment specific to the electrical instability before using a treatment specific to the mechanical instability; and
(h) if the patient's myocardium is less electrically unstable than mechanically unstable, treat the mechanical instability first, wherein treating the mechanical instability first comprises using a treatment specific to the mechanical instability before using a treatment specific to the electrical instability.

10. The computer readable medium of claim 9, wherein the IMD uses an algorithm to determine the myocardial electro-mechanical stability score, where the algorithm treats myocardial electrical stability and myocardial mechanical stability as being independent risk factors.

11. The computer readable medium of claim 9, wherein the one or more signals indicative of electrical functioning of the patient's heart include an intra cardiac electrogram signal and the one or more signals indicative of mechanical functioning of the patient's heart include a pressure signal.

12. The computer readable medium of claim 9, wherein the one or more signals indicative of electrical functioning of the patient's heart include intra cardiac electrogram signal, and the one or more further signals indicative of mechanical functioning of the patient's heart include at least one of the following:
a signal representative of ventricular pressure obtained from a pressure transducer within a ventricle;
a signal representative of contraction strength obtained from an accelerometer;
a signal representative of blood flow rate obtained from a blood flow transducer;
a signal representative of heart sounds obtained from a microphone or an accelerometer that responds to acoustic vibrations transmitted through body fluids;
a signal representative of blood volume obtained using an impedance measuring circuit;
a signal representative of pulse pressure obtained using a photo-plethysmography sensor; and
a signal representative of venous oxygen saturation obtained using an SVO2 sensor.

13. The computer readable medium of claim 9, wherein the instructions select from at least two different responses, wherein:
the responses involve different types of cardiac therapy,
at least a first response is specific to the myocardial electrical stability of the patient, and
at least a second response is specific to the myocardial mechanical stability of the patient.

14. The computer readable medium of claim 9, wherein the instructions select from at least two different responses, wherein:
the responses involve notifying different types of caregivers,
at least a first response comprises notifying a first caregiver specializing in treating a condition indicated by myocardial electrical instability, and
at least a second response comprises notifying a second, different caregiver specializing in treating a condition indicated by myocardial mechanical instability.

15. The computer readable medium of claim 14, wherein at least an electro-physiologist is notified if the myocardial electrical stability of the patient indicates that the patient is at an increased risk of arrhythmia, and
at least a heart failure specialist is notified if the myocardial mechanical stability of the patient indicates that the patient is at an increased risk of an acute heart failure exacerbation.

16. The computer readable medium of claim 9, wherein the response is specific to both the degree of electrical alternans and the degree of mechanical alternans.

17. The computer readable medium of claim 9, wherein the instruction further cause the processor to:
trigger a first response if electrical alternans are present but mechanical alternans are not present;
trigger a second response, that is different from the first response, if mechanical alternans are present but electrical alternans are not present; and
trigger a third response if both electrical and mechanical alternans are present.

18. The computer readable medium of claim 17, wherein the first, second and third responses involve delivering types of cardiac therapy.

19. The computer readable medium of claim 17, wherein the first, second and third responses involve notifying types of caregivers.

20. The computer readable medium of claim 9, wherein the instruction further cause the processor to:
monitor the patient's myocardial ischemic burden based on the one or more signals indicative of electrical functioning of the patient's heart; and
monitor the patient's risk of an adverse cardiac event based on the myocardial ischemic burden and the myocardial electro-mechanical stability score.

21. The computer readable medium of claim 20, wherein the instruction further cause the processor to: (d) trigger a response when the patient is at risk of an adverse cardiac event, where the response is based on the myocardial ischemic burden and the myocardial electro-mechanical stability score.

22. A method for determining a patient's myocardial electro-mechanical stability, comprising:
(a) obtaining one or more signals indicative of electrical functioning of a patient's heart, and one or more signals indicative of mechanical functioning of the patient's heart;
(b) determining the patient's myocardial index of electrical stability by determining a degree of electrical alternans based on the one or more signals indicative of electrical functioning of the patient's heart;
(c) determining the patient's myocardial index of mechanical stability by determining at least three degrees of mechanical alternans using a plurality of thresholds based on the one or more signals indicative of mechanical functioning of the patient's heart;
(d) using an algorithm to determine a myocardial electro-mechanical stability score by combining the patient's myocardial index of electrical stability and the patient's index of myocardial mechanical stability;
(e) determining whether the patient is at risk of an adverse cardiac event based on the myocardial electro-mechanical stability score;
(f) when the patient is at risk of an adverse cardiac event, triggering a response that is specific to both the myocardial electrical stability and the myocardial mechanical stability of the patient
(g) using an algorithm to determine whether the patient's myocardium is more electrically unstable or mechanically unstable;
(h) if the patient's myocardium is more electrically unstable than mechanically unstable, treating the electrical instability first, wherein treating the electrical instability first comprises using a treatment specific to the electrical instability before using a treatment specific to the mechanical instability; and
(i) if the patient's myocardium is less electrically unstable than mechanically unstable, treating the mechanical instability first, wherein treating the mechanical instability first comprises using a treatment specific to the mechanical instability before using a treatment specific to the electrical instability.

23. The method of claim 22, wherein step (d), where the algorithm treats myocardial electrical stability and myocardial mechanical stability as being independent risk factors and the patient's myocardial index of electrical stability and the patient's index of myocardial mechanical stability are added.

24. The method of claim 22, wherein the myocardial electro-mechanical stability score is indicative of the patient's risk of an arrhythmia and an acute heart failure exacerbation.

25. The method of claim 22, further comprising:
(e) triggering a response, wherein the response improves the patient's myocardial electrical stability without adversely affecting the patient's myocardial mechanical stability.

26. The method of claim 22, further comprising:
(e) triggering a response, wherein the response improves the patient's myocardial mechanical stability without adversely affecting the patient's electrical mechanical stability.

* * * * *